(12) United States Patent
Brendel et al.

(10) Patent No.: US 10,485,501 B2
(45) Date of Patent: Nov. 26, 2019

(54) COMPUTER TOMOGRAPHY X-RAY IMAGING

(71) Applicant: KONINKLIJKE PHILIPS N.V., Eindhoven (NL)

(72) Inventors: Bernhard Johannes Brendel, Norderstedt (DE); Thomas Koehler, Norderstedt (DE); Roland Proksa, Neu Wulmstorf (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 15/762,114

(22) PCT Filed: Sep. 4, 2017

(86) PCT No.: PCT/EP2017/072039
§ 371 (c)(1),
(2) Date: Mar. 22, 2018

(87) PCT Pub. No.: WO2018/046414
PCT Pub. Date: Mar. 15, 2018

(65) Prior Publication Data
US 2019/0183443 A1    Jun. 20, 2019

(30) Foreign Application Priority Data

Sep. 9, 2016 (EP) .................................... 16187966

(51) Int. Cl.
*G06K 9/40* (2006.01)
*G06K 9/00* (2006.01)
(Continued)

(52) U.S. Cl.
CPC .............. *A61B 6/482* (2013.01); *A61B 6/032* (2013.01); *A61B 6/4241* (2013.01);
(Continued)

(58) Field of Classification Search
CPC .... G06T 11/005; G06T 11/006; G06T 11/008; G06T 2207/10072; G06T 2211/40; A61B 6/50; A61B 6/5217
See application file for complete search history.

(56) References Cited

U.S. PATENT DOCUMENTS 7,194,061 B2    3/2007  Fujita
2009/0304142 A1  12/2009 Riumi
(Continued)

FOREIGN PATENT DOCUMENTS

CN    1284659 A    2/2001
WO   2015/011587   1/2015

*Primary Examiner* — Don K Wong
(74) *Attorney, Agent, or Firm* — Larry Liberchuk

(57) ABSTRACT

The present invention relates to computer tomography X-ray imaging. In order to provide further improved data for the reconstruction, a system (10) for computer tomography X-ray imaging is provided. The system comprises a data interface (12) and a processing unit (14). The data interface is configured to provide at least first and second CT X-ray radiation projection data for at least a first and second X-ray energy range, which ranges are different from each other. The processing unit is configured to determine a correction for slice normalization, and to apply an equal slice normalization for the first and the second CT X-ray projection data and thereby generating prepared first and second CT X-ray projection data. For the correction, the equal slice normalization is based on measured data of outer detector elements. Further, the data interface is configured to provide the prepared first and second CT X-ray projection data for further processing. In an example, the system further comprises a computer tomography X-ray imaging acquisition arrangement (20) with an X-ray source (22) configured to generate an X-ray beam, and an X-ray detector (26) configured as an energy discriminating X-ray detector to simultaneously provide X-ray radiation projection data for at least
(Continued)

two different X-ray energy ranges separately. The computer tomography X-ray imaging acquisition arrangement is configured to acquire at least the first and second CT X-ray projection data of a region of interest of an object for the at least first and second X-ray energy range.

13 Claims, 2 Drawing Sheets

(51) Int. Cl.
    *A61B 6/00*         (2006.01)
    *G06T 11/00*       (2006.01)
    *A61B 6/03*         (2006.01)

(52) U.S. Cl.
    CPC .......... *A61B 6/5211* (2013.01); *G06T 11/003* (2013.01); *G06T 2207/10081* (2013.01); *G06T 2211/408* (2013.01)

(56) References Cited

U.S. PATENT DOCUMENTS

| | | | |
|---|---|---|---|
| 2012/0314922 A1* | 12/2012 | Hsieh | G06T 11/008 382/131 |
| 2015/0178958 A1 | 6/2015 | Zou | |
| 2016/0038108 A1 | 2/2016 | Tamura | |
| 2016/0131774 A1 | 5/2016 | Lage | |
| 2016/0166229 A1 | 6/2016 | Matthews | |
| 2016/0209337 A1 | 7/2016 | Wang | |
| 2016/0225169 A1 | 8/2016 | Bippus | |

\* cited by examiner

COMPUTER TOMOGRAPHY X-RAY IMAGING

CROSS REFERENCE TO RELATED APPLICATIONS

This application is the U.S. National Phase application under 35 U.S.C. § 371 of International Application No. PCT/EP2017/072039, filed Sep. 4, 2017, published as WO 2018/046414 on Mar. 15, 2018 which claims the benefit of European Patent Application Number 16187966.3 filed Sep. 9, 2016. These applications are hereby incorporated by reference herein.

FIELD OF THE INVENTION

The present invention relates to a system for computer tomography X-ray imaging and a method for computer tomography X-ray imaging as well as to a computer program element for controlling an apparatus and a computer readable medium.

BACKGROUND OF THE INVENTION

In spectral computer tomography (CT), X-ray radiation is detected for several energy levels or ranges to provide enhanced image projection data for reconstructing an image. In spectral CT imaging, when combining several projection data images, as a pre-processing procedure, an adaptation may be provided. For example, US 2016/0225169 describes a method for local adjustment of regularization parameters for image quality optimization in fully 3D iterative CT reconstruction. This may be based on image measurement and has the aim of compensating differences. However, it has been shown that this may be subject to noise.

SUMMARY OF THE INVENTION

There may be a need to provide further improved data for the reconstruction.

The object of the present invention is solved by the subject-matter of the independent claims; further embodiments are incorporated in the dependent claims. It should be noted that the following described aspects of the invention apply also for the system for computer tomography X-ray imaging and the method for computer tomography X-ray imaging as well as for the computer program element for controlling an apparatus and for the computer readable medium.

According to the present invention, a system for computer tomography X-ray imaging is provided. The system comprises a data interface, and a processing unit. The data interface is configured to provide at least first and second CT X-ray radiation projection data of an object for at least a first and second X-ray energy range, which ranges are different from each other. The at least first and second CT X-ray radiation projection data of the object comprises a plurality of slices of X-ray measurements from different angles to produce cross-sectional images of the object. The processing unit is configured to determine a correction for slice normalization of the plurality of slices of X-ray measurements to change the first and the second CT X-ray projection data in terms of their pixel intensity values. The processing unit is also configured to apply an equal slice normalization for the first and the second CT X-ray projection data, wherein the pixel intensity values of the plurality of slices of X-ray measurements in the slice normalization is changeable such that a reference to a predetermined value is provided, and thereby to generate prepared first and second CT X-ray projection data. For the correction, the equal slice normalization is based on measured data of detector measurements from detector areas detecting X-ray radiation that is uninfluenced by the object arranged in the radiation path between X-ray source and X-ray detector during imaging. Further, the data interface is configured to provide the prepared first and second CT X-ray projection data for further processing.

The term "un-influenced" relates to a purposely missing influence, i.e. a missing attenuation. Hence, the X-ray radiation is not attenuated by the object, for example a patient. The X-ray radiation is also not attenuated by other objects, such as holding and support arrangements for patient or equipment.

In other words, for the correction, the equal slice normalization is based on measured data of detector measurements not influenced by an object arranged in the radiation path during imaging.

This means that, for the correction, the measured data of those detector measurements is provided for the basis of the equal slice normalization, which measurements result from detector areas with direct sight to the X-ray source during CT X-ray projection data acquisition, i.e. during X-ray image data acquisition.

The measured data, on which the normalization is based, is acquired during the actual imaging scan, i.e. at the same time as the image data of the object, but detected outside the detector area detecting the image data of the object.

Briefly said, for the correction, the measured data of detector measurements used for the basis of the equal slice normalization results from areas with non-attenuated X-ray radiation. The term "non-attenuated" relates to X-ray radiation that is essentially un-attenuated, i.e. the radiation does not pass any relevant objects such as a patient. Of course, the radiation may pass through substantially X-ray transparent materials, for example used for housings or covers, cloths and support surfaces, and of course through air.

The term "equal" relates to applying the same normalization in form of the correction fro both energy ranges, i.e. for the first and the second X-ray energy range.

In an example, a system for computer tomography X-ray imaging is provided. The system comprises a data interface, and a processing unit. The data interface is configured to provide at least first and second CT X-ray radiation projection data for at least a first and second X-ray energy range, which ranges are different from each other. The processing unit is configured to determine a correction for slice normalization. The processing unit is also configured to apply an equal slice normalization for the first and the second CT X-ray projection data and thereby generating prepared first and second CT X-ray projection data. For the correction, the equal slice normalization is based on measured data of detector measurements not influenced by an object, e.g. data from outer detector elements. Further, the data interface is configured to provide the prepared first and second CT X-ray projection data for further processing.

Thereby, slice normalization is performed, for example to compensate for tube flux fluctuations. Advantageously, the slice normalization processing for the different energy ranges results in less difference between measurements, and leads to improved results when reconstructing the image on behalf of the corrected or normalized projection data. It also improves to reduce artifacts caused e.g. by outer detector elements being affected by the patient or any other object inside the system. Due to providing equal normalization, the need to check if an object influence is detected, which might lead to the need to turn off slice normalization procedure, which would result in abrupt changes in prepped data, the procedure based on the present invention is less prone to error and the provided data is more consistent data and artefacts are reduced.

The term "slice" relates to the plurality of acquired data that is acquired as adjacent slices in CT to cover ideally the complete volume of the region of interest. The result is a 3D dataset, which is then used for projection to achieve visualization.

The term "normalization" relates to a process in image processing where the range of pixel intensity values is changed. For example, the range is changed such that the pixel intensity values are aligned with a predetermined standard pixel intensity value for a predetermined radiation attenuation. In another example, the range is changed to improve further image processing procedures, for example, contrast can be enhanced by the normalization.

The term "slice normalization" relates to normalization of the measured slices in CT, i.e. measured data before reconstruction for visualization. The "predetermined" value may be provided as a standardized value. Thus, the normalization enables to change the range of the measured pixel intensity values in an optimizing way to allow improved use of the information content, i.e. for the reconstruction process in CT. The "predetermined" value can be a value defined for a particular system set-up, or for a particular examination or intervention set-up (type) or for a particular type of reconstruction in CT. The "predetermined" value can also be a standardized value commonly used.

According to an example, the measured data provided by the detector measurements used for the basis of the equal slice normalization results from areas of a detector outside the projection of the object such that the X-ray radiation directly reaches the detector.

According to an example, the measured data is provided by outer detector elements.

The term "outer detector elements relates" to detector elements arranged outside the main (or center) portions of the detector, which center portions are provided for detecting radiation transmitted through the patient/object. The term "outer" is relative to the detector portion provided for projection of the object. Depending on the size of the detector, the "outer" detector elements may be on the peripheral (when nearly all of the detector's surface is used for image data acquisition. If only a smaller part of the detector is used for projecting the object, the "outer" detector elements may be detector areas within the detector's surface area.

According to an example, the system further comprises a computer tomography X-ray imaging acquisition arrangement with an X-ray source configured to generate an X-ray beam, and an X-ray detector configured as an energy discriminating X-ray detector to simultaneously provide X-ray radiation projection data for at least two different X-ray energy ranges separately. The computer tomography X-ray imaging acquisition arrangement is configured to acquire at least the first and second CT X-ray projection data of a region of interest of the object for the at least first and second X-ray energy range.

According to an example, the energy discriminating X-ray detector is a dual layer X-ray detector with a first detector layer and a second detector layer, wherein the first and second detector layers being arranged behind each other in relation to the X-ray source, and the first and second detector layers being configured to simultaneously provide the X-ray projection data for the at least two different X-ray energy ranges.

According to an example, the energy discriminating X-ray detector is a photon counting detector counting photons for different energies.

According to the present invention, also a method for computer tomography X-ray imaging is provided. The method comprises the following steps:
a) acquiring CT X-ray projection data of a region of interest of an object with at least a first and a second X-ray energy range being different from each other; wherein the at least first and second CT X-ray radiation projection data of the object comprises a plurality of slices of X-ray measurements from different angles to produce cross-sectional images of the object
b) determining a correction factor for slice normalization of the plurality of slices of X-ray measurements to change the first and the second CT X-ray projection data in terms of their pixel intensity values;
c) applying an equal slice normalization for the first and the second CT X-ray projection data and thereby generating prepared first and second CT X-ray projection data; and
d) providing the prepared first and second CT X-ray projection data for further processing.

wherein, for step b), the equal slice normalization is based on measured data of detector measurements from detector areas detecting X-ray radiation that is uninfluenced by the object arranged in the radiation path between X-ray source and X-ray detector during imaging.

According to an example, a method for computer tomography X-ray imaging is provided. The method comprises the following steps:
a) acquiring CT X-ray projection data of a region of interest of an object with at least a first and a second X-ray energy range being different from each other;
b) determining a correction factor for slice normalization;
c) applying an equal slice normalization for the first and the second CT X-ray projection data and thereby generating prepared first and second CT X-ray projection data; and
d) providing the prepared first and second CT X-ray projection data for further processing.

wherein, for step b), the equal slice normalization is based on measured data of detector measurements not influenced by an object, e.g. outer detector elements.

According to an example, the measured data provided by the detector measurements used for the basis of the equal slice normalization is resulting from areas of a detector outside the projection of the object such that the X-ray radiation directly reaches the detector.

According to an example, the measured data is provided by outer detector elements.

According to an example, before step a), it is provided a step of a1), acquiring CT X-ray projection data of a region of interest of an object with at least the first and the second X-ray energy range with an energy discriminating X-ray detector.

According to an example, for step b), measured data of the outer detector elements is provided for each energy level range and a mean value is determined for the correction for the slice normalization.

According to another example, for step b), measured data of the outer detector elements is provided for each energy level range and a measured value of either the first or the second energy level range is determined for the correction for the slice normalization.

According to an aspect, equal normalization is provided for two (or more) energy ranges of projected image data. One option to achieve a consistent processing of the two detector layers is to use the mean of the measured data of outer detector elements of upper and lower detector layer to determine the slice normalization-rescaling for both layers. Another option is to use only the measured data of one of the two layers to determine the slice normalization-rescaling for both layers. The measured data forming the basis of the normalization may vary due to different X-ray intensity output of the X-ray source. As the data is measured in areas outside the part of the radiation radiating through the patient, the measured radiation can be taken and put into relation to a standardized intensity value. The resulting normalization thus considers a possible change in intensity of the radiation from the X-ray tube, such as caused by flux intensity variations of an X-ray tube, and results in improved data for the reconstruction.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
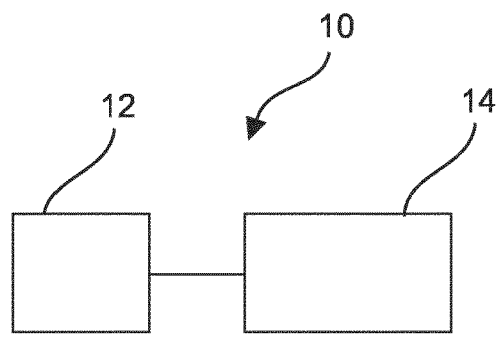
FIG. 1 shows a schematic overview of a system for computer tomography X-ray imaging.

FIG. 1 shows a system 10 for computer tomography X-ray imaging. The system 10 comprises a data interface 12, and a processing unit 14. The data interface 12 is configured to provide at least first and second CT X-ray radiation projection data of an object for at least a first and second X-ray energy range. The ranges are different from each other. The at least first and second CT X-ray radiation projection data of the object comprises a plurality of slices of X-ray measurements from different angles to produce cross-sectional images of the object. The processing unit 14 is configured to determine a correction for slice normalization of the plurality of slices of X-ray measurements to change the first and the second CT X-ray projection data in terms of their pixel intensity values. The processing unit 14 is also configured to apply an equal slice normalization for the first and the second CT X-ray projection data, wherein the pixel intensity values of the plurality of slices of X-ray measurements in the slice normalization is changeable such that a reference to a predetermined value is provided, and thereby to generate prepared first and second CT X-ray projection data. For the correction, the equal slice normalization is based on measured data of detector measurements from detector areas detecting X-ray radiation that is uninfluenced by the object arranged in the radiation path between X-ray source and X-ray detector during imaging. Further, the data interface 12 is configured to provide the prepared first and second CT X-ray projection data for further processing.

The abbreviation CT refers to computer tomography X-ray imaging.

The term "being different from each other" relates to ranges or values that are separate from each other, or that are adjacent or ranges that are partly overlapping, or ranges that are completely overlapping, but with different contributions off the different regions of the ranges.

The further processing, e.g. image processing, may be image reconstruction steps for generating two- or three-dimensional CT X-ray images. The images are thus reconstructed from the corrected projection data.

The term "correction" relates to the correction applied to the projection data. The correction may be provided as a correction value or a correction factor or even a correction term. The correction may be applied to the log intensity or the intensity.

In an example, the measured data provided by the detector measurements used for the basis of the equal slice normalization results from areas of a detector outside the projection of the object such that the X-ray radiation directly reaches the detector.

In an option, the measured data is provided by outer detector elements

In an example, for the correction, a correction factor is provided that is multiplied with the measured intensities.

In an example, for the correction, a correction value is provided that is added to or subtracted from the log intensities.

In an example, for the correction, a slice normalization correction is determined for each "view" individually, with a view being the at least two projections for the at least two different energy ranges acquired for the same position and orientation of source and detector.

Figure 2:
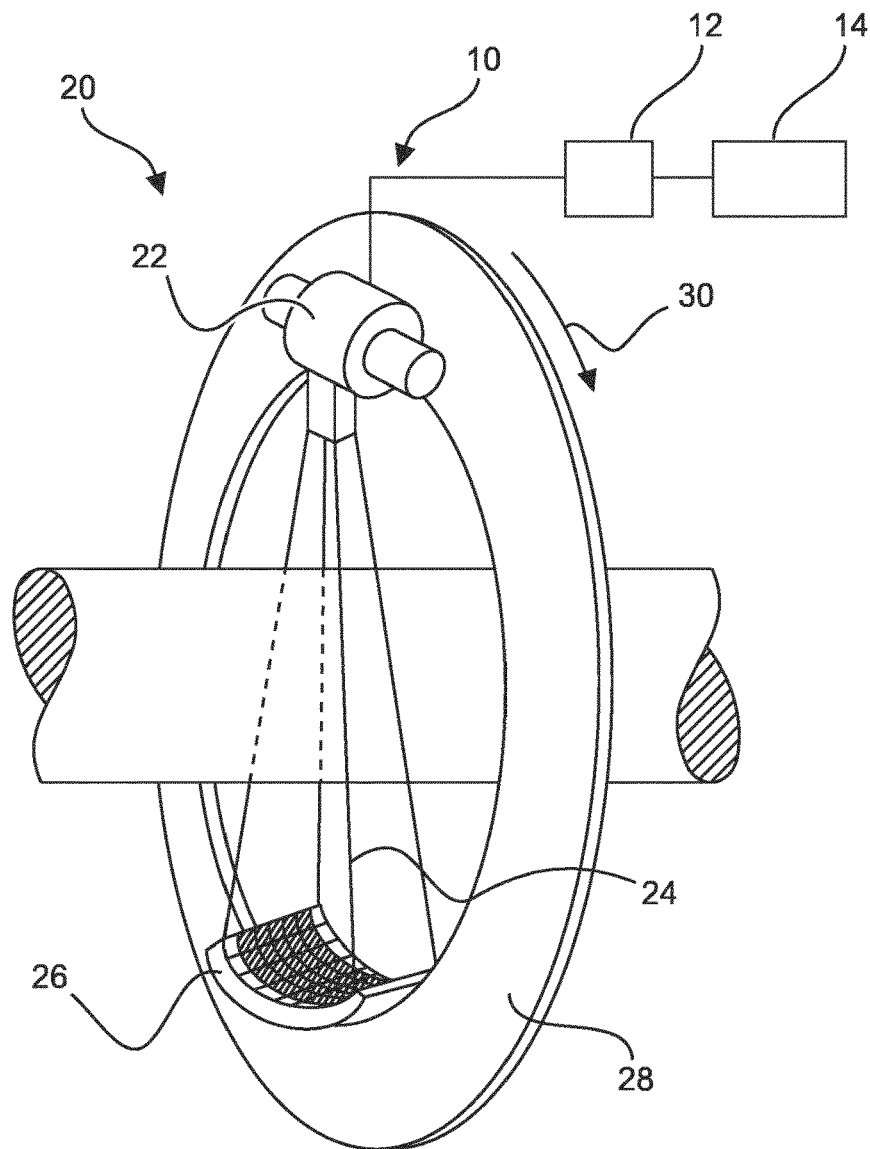
FIG. 2 shows another example of the system with a computer tomography X-ray imaging acquisition arrangement.

FIG. 2 shows an example that further comprises a computer tomography X-ray imaging acquisition arrangement 20 with an X-ray source 22 configured to generate an X-ray beam 24, and an X-ray detector 26 configured as an energy discriminating X-ray detector to simultaneously provide X-ray radiation projection data for at least two different X-ray energy ranges separately. The computer tomography X-ray imaging acquisition arrangement 20 is configured to acquire at least the first and second CT X-ray projection data of a region of interest of an object for the at least first and second X-ray energy range.

The X-ray source 22 and the X-ray detector 26 are rotatably mounted to a gantry 28. In fixed relation to each other, they can rotate around the gantry, which is indicated by arrow 20. In an example, the X-ray source provides a cone-shaped X-ray beam or a fan-shaped X-ray beam. Depending on the X-ray beam, a respective array of detector elements or a line-detector is provided.

In the case of a fan-shaped beam, the term "slices" relates to the data acquired in form of slices (resulting from the fan-shaped beam radiating the object).

In the case of a cone-shaped beam, instead of slices, X-ray attenuation image data is provided that is then used for reconstruction. Hence, the term "slices" also relate to the raw images acquired with cone-shaped X-ray radiation.

The data interface 12 and the processing unit 14 are data-connected to the X-ray imaging acquisition arrangement 20, which is indicated by a line connection. Of course, this connection can be a wire connection or also a wireless connection. Further supply is not shown, such as energy supply or data supply for controlling the system. It is noted that the data interface 12 and the processing unit 14 are of course also connected to the X-ray detector 26.

The term "energy discriminating" relates to a detector capable of detecting X-ray radiation with different energies and to provide this data simultaneously. The object is hence radiated with X-ray radiation comprising energy in different ranges.

The energy discriminating X-ray detector may be a dual layer X-ray detector with a first detector layer and a second detector layer. The first and second detector layers are arranged behind each other in relation to the X-ray source, and the first and second detector layers are configured to simultaneously provide the X-ray projection data for the at least two different X-ray energy ranges.

The energy discriminating X-ray detector may be provided as a multi-layer detector, for example, with more than two layers, for example as three-layer detector.

In another example, the energy discriminating X-ray detector is a photon counting detector counting photons for different energies.

Figure 3:
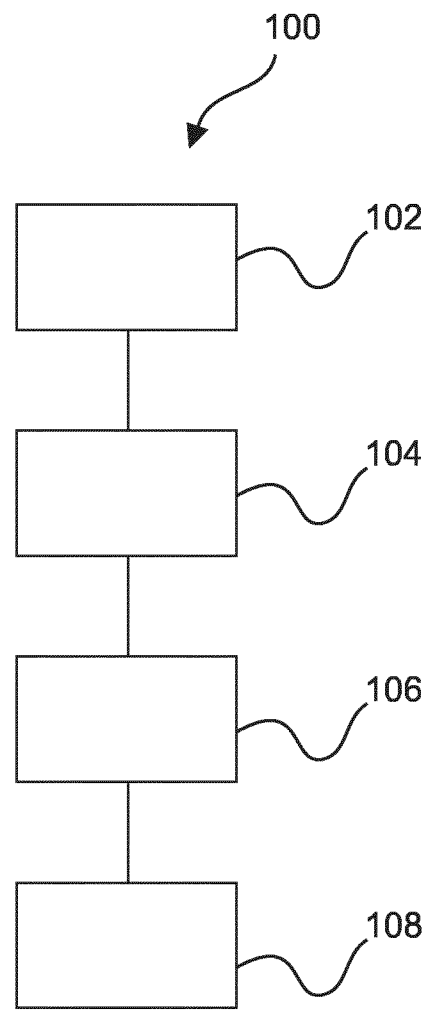
FIG. 3 shows steps of an example of a method for computer tomography X-ray imaging.

FIG. 3 shows an example of steps of a method 100 for computer tomography X-ray imaging. In a first step 102, also referred to as step a), CT X-ray projection data of a region of interest of an object with at least a first and a second X-ray energy range being different from each other is acquired. The at least first and second CT X-ray radiation projection data of the object comprises a plurality of slices of X-ray measurements from different angles to produce cross-sectional images of the object. In a second step 104, also referred to as step b), a correction factor for slice normalization of the plurality of slices of X-ray measurements to change the first and the second CT X-ray projection data in terms of their pixel intensity values is determined. In a third step 106, also referred to as step c), equal slice normalization is applied for the first and the second CT X-ray projection data and thereby prepared first and second CT X-ray projection data are generated. In a fourth step 108, also referred to as step d), the prepared first and second CT X-ray projection data are provided for further processing. For step b), the equal slice normalization is based on measured data of detector measurements from detector areas detecting X-ray radiation that is uninfluenced by an object arranged in the radiation path between X-ray source and X-ray detector during imaging.

In an example, the measured data provided by the detector measurements used for the basis of the equal slice normalization is resulting from areas of a detector outside the projection of the object such that the X-ray radiation directly reaches the detector.

In an option, the measured data is provided by outer detector elements.

As an option, indicated by hashed lines, before step a), it is provided an initial step 110 of a1), acquiring CT X-ray projection data of a region of interest of an object with at least the first and the second X-ray energy range with an energy discriminating X-ray detector.

In an example, in step a), the X-ray projection data is acquired by a dual layer X-ray detector providing the first X-ray projection data with the first X-ray energy range in a first layer and the second X-ray projection data with the second X-ray energy range in a second layer of the dual layer X-ray detector.

In an example, following step d) it is provided a step e) of image reconstructing to provide a three-dimensional X-ray image of the region of interest of the object.

According to an example, not further shown in detail, for step b), measured data of the outer detector elements is provided for each energy level range and a mean value is determined for the correction for the slice normalization.

In the example of a dual layer, the data is measured for the outer detector elements in the first and in the second layer.

According to another example, also not further shown in detail, for step b), measured data of the outer detector elements is provided for each energy level range and a measured value of either the first or the second energy level range is determined for the correction for the slice normalization.

According to an example, for step c), a correction factor is provided that is multiplied with the measured intensities.

According to an example, for step c), a correction value is provided that is added to or subtracted from the log intensities.

In an example, for step c), a slice normalization correction is determined for each "view" individually, with a view being the at least two projections for the at least two different energy ranges acquired for the same position and orientation of source and detector.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for computer tomography X-ray imaging, the system comprising:
   a data interface; and
   a processing unit;
   wherein the data interface is configured to provide at least first and second CT X-ray radiation projection data of an object for at least a first and second X-ray energy range, which ranges are different from each other;
   wherein the at least first and second CT X-ray radiation projection data of the object comprises a plurality of slices of X-ray measurements from different angles to produce cross-sectional images of the object;
   wherein the processing unit is configured to determine a correction for slice normalization of the plurality of slices of X-ray measurements to change the first and the second CT X-ray projection data in terms of their pixel intensity values; and to apply an equal slice normalization for the first and the second CT X-ray projection data, wherein the pixel intensity values of the plurality of slices of X-ray measurements in the slice normalization is changeable such that a reference to a predetermined value is provided, and thereby to generate prepared first and second CT X-ray projection data;
   wherein, for the correction, the equal slice normalization is based on measured data of detector measurements from detector areas detecting X-ray radiation that is uninfluenced by the object arranged in the radiation path between X-ray source and X-ray detector during imaging; and
   wherein the data interface is configured to provide the prepared first and second CT X-ray projection data for further processing.

2. The system according to claim 1, wherein the measured data provided by the detector measurements used for the basis of the equal slice normalization results from areas of a detector outside the projection of the object such that the X-ray radiation directly reaches the detector; and
   wherein, preferably, the measured data is provided by outer detector elements.

3. The system according to claim 1, wherein the system further comprises a computer tomography X-ray imaging acquisition arrangement with:
   an X-ray source configured to generate an X-ray beam, and
   an X-ray detector configured as an energy discriminating X-ray detector to simultaneously provide X-ray radiation projection data for at least two different X-ray energy ranges separately;
   wherein the computer tomography X-ray imaging acquisition arrangement is configured to acquire at least the first and second CT X-ray projection data of a region of interest of the object for the at least first and second X-ray energy range.

4. The system according to claim 3, wherein the energy discriminating X-ray detector is a dual layer X-ray detector with a first detector layer and a second detector layer, wherein the first and second detector layers being arranged behind each other in relation to the X-ray source, and the first and second detector layers being configured to simultaneously provide the X-ray projection data for the at least two different X-ray energy ranges.

5. The system according to claim 3, wherein the energy discriminating X-ray detector is a photon counting detector counting photons for different energies.

6. A method for computer tomography X-ray imaging, the method comprising the following steps:
   a) acquiring CT X-ray projection data of a region of interest of an object with at least a first and a second X-ray energy range being different from each other;
   wherein the at least first and second CT X-ray radiation projection data of the object comprises a plurality of slices of X-ray measurements from different angles to produce cross-sectional images of the object;
   b) determining a correction factor for slice normalization of the plurality of slices of X-ray measurements to change the first and the second CT X-ray projection data in terms of their pixel intensity values;
   c) applying an equal slice normalization for the first and the second CT X-ray projection data, and thereby generating prepared first and second CT X-ray projection data; and
   d) providing the prepared first and second CT X-ray projection data for further processing;
   wherein, for step b), the equal slice normalization is based on measured data of detector measurements from detector areas detecting X-ray radiation that is uninfluenced by the object arranged in the radiation path between X-ray source and X-ray detector during imaging.

7. The method according to claim 6, wherein the measured data provided by the detector measurements used for the basis of the equal slice normalization is resulting from areas of a detector outside the projection of the object such that the X-ray radiation directly reaches the detector; and
   wherein, preferably, the measured data is provided by outer detector elements.

8. The method according to claim 6, wherein, before step a) it is provided a step of:
   acquiring CT X-ray projection data of a region of interest of an object with at least the first and the second X-ray energy range with an energy discriminating X-ray detector.

9. The method according to claim 7, wherein for step b), measured data of the outer detector elements is provided for each energy level range and a mean value is determined for the correction for the slice normalization.

10. The method according to claim 7, wherein for step b), measured data of the outer detector elements is provided for each energy level range and a measured value of either the first or the second energy level range is determined for the correction for the slice normalization.

11. The method according to claim 6, wherein for step c):
i) a correction factor is provided that is multiplied with the measured intensities; and/or
ii) a correction value is provided that is added to or subtracted from the log intensities.

12. A computer program element for controlling an apparatus, which, when being executed by a processing unit, is adapted to perform the method step of claim 6.

13. A computer readable medium having stored the program element of claim 12.

\* \* \* \* \*